(12) United States Patent
Boulware et al.

(10) Patent No.: US 9,759,691 B2
(45) Date of Patent: Sep. 12, 2017

(54) GATING METHODS FOR USE IN WELD INSPECTION SYSTEMS

(71) Applicant: EDISON WELDING INSTITUTE, INC., Columbus, OH (US)

(72) Inventors: Paul C. Boulware, Columbus, OH (US); Roger Spencer, Asheville, OH (US); Jeong K. Na, Centerville, OH (US)

(73) Assignee: Cumberland & Western Resources, LLC, Bowling Green, KY (US)

( * ) Notice: Subject to any disclaimer, the term of this patent is extended or adjusted under 35 U.S.C. 154(b) by 0 days.

(21) Appl. No.: 15/133,642

(22) Filed: Apr. 20, 2016

(65) Prior Publication Data
US 2016/0231291 A1 Aug. 11, 2016

Related U.S. Application Data

(63) Continuation-in-part of application No. 13/468,502, filed on May 10, 2012, now Pat. No. 9,063,059, and
(Continued)

(51) Int. Cl.
*G01M 7/00* (2006.01)
*G01N 29/26* (2006.01)
(Continued)

(52) U.S. Cl.
CPC ....... *G01N 29/262* (2013.01); *G01N 29/0645* (2013.01); *G01N 29/24* (2013.01);
(Continued)

(58) Field of Classification Search
CPC ................. G01N 29/075; G01N 29/24; G01N 2291/0234; G01N 2291/2672;
(Continued)

(56) References Cited

U.S. PATENT DOCUMENTS 3,895,685 A * 7/1975 Gillette .................... B41J 2/285
181/5
4,534,221 A * 8/1985 Fife ...................... G01S 15/8922
73/599
(Continued)

OTHER PUBLICATIONS

International Search Report and Written Opinion of the International Searching Authority received in PCT/US2016/28393, mailed Aug. 31, 2016.

*Primary Examiner* — Laura Martin
*Assistant Examiner* — Samir M Shah
(74) *Attorney, Agent, or Firm* — Frost Brown Todd LLC

(57) ABSTRACT

A method for characterizing a spot weld, including acquiring a sequence of A-scans from an ultrasonic phased array, wherein the A-scans describe individual portions of a field of view of the phased array; manually applying an interface gate and a flaw gate to each individual A-scan within the sequence of A-scans; calculating a gate ratio between a maximum amplitude under the interface gate and a maximum amplitude under the flaw gate for each individual A-scan; plotting the gate ratio for each individual A-scan as a function of location within the phased array field of view to generate a weld fusion map; using a predetermined threshold to differentiate fused locations from unfused locations on the weld fusion map; and calculating predetermined weld metrics, wherein the predetermined weld metrics include area, diameter, width, length, percent fused, or combinations thereof.

7 Claims, 16 Drawing Sheets

Related U.S. Application Data a continuation-in-part of application No. 14/183,643, filed on Feb. 19, 2014, now Pat. No. 9,037,419.

(60) Provisional application No. 62/150,084, filed on Apr. 20, 2015, provisional application No. 61/484,312, filed on May 10, 2011.

(51) Int. Cl.
*G01N 29/24* (2006.01)
*G01N 29/06* (2006.01)
*G01N 29/28* (2006.01)

(52) U.S. Cl.
CPC ....... *G01N 29/28* (2013.01); *G01N 2291/106* (2013.01); *G01N 2291/2672* (2013.01)

(58) Field of Classification Search
CPC ......... G01N 2291/0289; G01N 29/262; G01N 29/30; G01N 29/0645; G01N 2291/2638
See application file for complete search history.

(56) References Cited

U.S. PATENT DOCUMENTS

| | | | |
|---|---|---|---|
| 5,677,490 A * | 10/1997 | Gunther | G01N 29/043 73/620 |
| 6,484,584 B2 * | 11/2002 | Johnson | B23K 31/125 73/624 |
| 6,925,882 B1 * | 8/2005 | Fleming | B23K 31/12 73/632 |
| 6,948,369 B2 * | 9/2005 | Fleming | G01N 3/00 228/104 |
| 6,957,583 B2 * | 10/2005 | Tooma | B06B 1/06 600/448 |
| 7,021,143 B2 * | 4/2006 | Dasch | G01N 29/225 73/620 |
| 8,206,305 B2 * | 6/2012 | Garbini | A61B 8/12 29/25.35 |
| 8,215,173 B2 * | 7/2012 | Spencer | G01N 29/069 73/620 |
| 2004/0118210 A1 * | 6/2004 | Tooma | B06B 1/06 73/625 |
| 2005/0126293 A1 * | 6/2005 | Dasch | G01N 29/225 73/618 |
| 2007/0038400 A1 * | 2/2007 | Lee | B23K 11/24 702/103 |
| 2009/0010459 A1 * | 1/2009 | Garbini | A61B 8/12 381/190 |
| 2010/0031750 A1 * | 2/2010 | Spencer | G01N 29/069 73/620 |
| 2012/0310551 A1 * | 12/2012 | Na | G01N 29/0645 702/39 |
| 2014/0165730 A1 * | 6/2014 | Na | G01N 29/0645 73/588 |
| 2014/0238136 A1 * | 8/2014 | Ten Grotenhuis | G01N 29/0654 73/592 |
| 2016/0231291 A1 * | 8/2016 | Boulware | G01N 29/262 |
| 2016/0320344 A1 * | 11/2016 | Spencer | G01N 29/043 |

* cited by examiner

THE ARROWS IN THE DIAGRAM REPRESENT HOW A SOUND WAVE TRANSMITS AND REFLECTS AT A MATERIAL'S INTERFACE.
A THINNER LINE REPRESENTS LOSS OF ACOUSTIC ENERGY AS THE SOUND WAVE INTERACTS WITH A SURFACE

3-Dimensional Array Element

■ Red Elements: 0 delay
■ Blue Elements: (n) nano-second delay
■ Green Element: (n+m) nano-second delay

GATING METHODS FOR USE IN WELD INSPECTION SYSTEMS

CROSS-REFERENCE TO RELATED APPLICATIONS

This patent application is a continuation-in-part of U.S. patent application Ser. No. 13/468,502 filed on May 10, 2012 and entitled "3-D Matrix Phased Array Spot Weld Inspection System", now U.S. Pat. No. 9,063,059, which claimed the benefit of U.S. Provisional Patent Application Ser. No. 61/484,312 filed on May 10, 2011 and entitled "Three-Dimensional Matrix Phased Array Spot Weld Inspection System", the disclosures of which are incorporated by reference herein in their entirety and made part of the present U.S. utility patent application for all purposes. This patent application is also a continuation-in-part of U.S. patent application Ser. No. 14/183,643 filed on Feb. 19, 2014 and entitled "Portable Matrix Phased Array Spot Weld Inspection System", now U.S. Pat. No. 9,037,419, which claimed the benefit of U.S. Provisional Patent Application Ser. No. 61/484,312 filed on May 10, 2011 and entitled "Three-Dimensional Matrix Phased Array Spot Weld Inspection System", the disclosures of which are incorporated by reference herein in their entirety and made part of the present U.S. utility patent application for all purposes. This patent application also claims the benefit of U.S. Provisional Patent Application Ser. No. 62/150,084 filed on Apr. 20, 2015 and entitled "Gating Methods for Use in Weld Inspection Systems," the disclosure of which is hereby incorporated by reference herein in its entirety and made part of the present U.S. utility patent application for all purposes.

BACKGROUND OF THE INVENTION

The present invention relates generally to inspection systems for use in assessing the performance of industrial manufacturing processes, and more specifically to a nondestructive inspection system for assessing the quality of resistance spot welds and other weld joints.

Sheet metal joining processes are widely used in many industries including the aerospace and automotive industries. Among these processes, resistance spot welding is a very common procedure used to join metal sheets because it has high process speed and is easily adopted in mass production lines. Seam welding, weld bonding, adhesive joining, soldering, and brazing have also gained acceptance. The quality control of such joining processes has been recognized as an important issue to manufacturers. The quality of weld joints is affected by the joining process itself and by the design of the joint. Many factors are considered, including metallurgic reactions, thermal behaviors, chemical composition, starting condition of the base metal, welding and bonding conditions, and the welding and bonding equipment used during the process. Furthermore, the intricate relationship between these factors makes it difficult to control the quality of the weld joint and difficult to inspect the weld joint in a nondestructive manner.

Acoustic methods are commonly used nondestructive testing methods for various inspection applications. Unlike other nondestructive testing methods, acoustic methods provide both surface and internal information. Moreover, acoustic methods allow for deeper penetration into specimens and higher sensitivity to small discontinuities in a weld joint. Acoustic methods, however, do have limitations. The most significant limitations include the requirement of a skillful operator for using the testing device and analyzing acoustic data, as well as the very subjective nature of identifying a stuck or cold weld or inadequate bond, such as a kissing bond. Accordingly, the field of ultrasonic nondestructive evaluation (NDE) is in need of a reliable system and method for identifying poor quality joints in a manner that eliminates the involvement of a skilled operator and the subjective interpretation of test data derived from the inspection. Furthermore, there is an ongoing need for an automated system for conducting weld inspection that provides rapid, efficient, and reliable characterization and evaluation of spot welds and other welds.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a method for characterizing owed is provided. This method includes providing an acoustic probe that further includes a plurality of ultrasonic transducer elements arranged in a curved array at one end of the acoustic probe, wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions; providing a phased array excitation unit in electrical communication with the array of transducer elements for ultrasonically exciting the transducer elements in a phased manner; providing a controller in electrical communication with the phased array excitation unit for controlling the operation of the phased array unit and gathering and processing information from the ultrasonic transducers; acquiring a sequence of A-scans from the phased array, wherein the A-scans describe individual portions of a field of view of the phased array; manually applying an interface gate and a flaw gate to each individual A-scan within the sequence of A-scans; calculating a gate ratio between a maximum amplitude under the interface gate and a maximum amplitude under the flaw gate for each individual A-scan; plotting the gate ratio for each individual A-scan as a function of location within the phased array field of view to generate a weld fusion map; using a predetermined threshold to differentiate fused locations from unfused locations on the weld fusion map; and calculating predetermined weld metrics, wherein the predetermined weld metrics include area, diameter, width, length, percent fused, or combinations thereof.

In accordance with another aspect of the present invention, a method for characterizing a spot weld is provided. This method includes providing an acoustic probe that further includes a plurality of ultrasonic transducer elements arranged in a curved array at one end of the acoustic probe, wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions; providing a phased array excitation unit in electrical communication with the array of transducer elements for ultrasonically exciting the transducer elements in a phased manner; providing a computerized controller in electrical communication with the phased array excitation unit for controlling the operation of the phased array unit and gathering and processing information from the ultrasonic transducers; acquiring a sequence of A-scans from the phased array, wherein the A-scans describe individual portions of a field of view of the phased array; defining an interface gate offset and length and a flaw gate offset and length with respect to a known total material thickness for each individual A-scan within the sequence of A-scans; calculating a gate ratio between a maximum amplitude under the interface gate and a maximum amplitude under the flaw gate for each individual A-scan; plotting the gate ratio for each individual A-scan as a function of location within the phased array field of view to generate a weld fusion map; using a predetermined threshold to differentiate fused locations from unfused locations on the weld fusion map; and calculating predetermined weld metrics; wherein the predetermined weld metrics include area, diameter, width, length, percent fused, or combinations thereof.

In yet another aspect of this invention, another method for characterizing a spot weld is provided. This method includes providing an acoustic probe that further includes a plurality of ultrasonic transducer elements arranged in a curved array at one end of the acoustic probe, wherein the transducer elements are operative to both generate ultrasonic signals and to receive reflections thereof; and a combination of materials for allowing the probe to conform to a contoured surface of the spot weld while enabling sound energy to be transferred directly into the spot weld under test conditions; providing a phased array excitation unit in electrical communication with the array of transducer elements for ultrasonically exciting the transducer elements in a phased manner; providing a computerized controller in electrical communication with the phased array excitation unit for controlling the operation of the phased array unit and gathering and processing information from the ultrasonic transducers; and measuring one-dimensional alignment of the acoustic probe, wherein measuring one-dimensional alignment of the acoustic probe further includes acquiring a sequence of A-scans from the phased array, wherein the A-scans describe individual portions of a field of view of the phased array; obtaining a maximum amplitude of a first front wall interface for each individual A-scan within an inner portion of the phased array field of view; determining the mean of the maximum amplitudes obtained; and using a lookup table to assign an alignment metric to the acoustic probe based on the mean of the maximum amplitudes. Another embodiment includes measuring two-dimensional alignment of the acoustic probe, wherein measuring two-dimensional alignment of the acoustic probe further includes acquiring a sequence of A-scans from the phased array, wherein the A-scans describe individual portions of a field of view of the phased array; obtaining a maximum amplitude and position of a first front wall interface for each individual A-scan within the phased array field of view; plotting each maximum amplitude as a function of location within the phased array field of view to generate an alignment map; and determining the centroid of the alignment map, wherein the resultant vector from the centroid to the origin determines an alignment metric in two dimensions.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein.

DETAILED DESCRIPTION OF THE INVENTION

Figure 1:
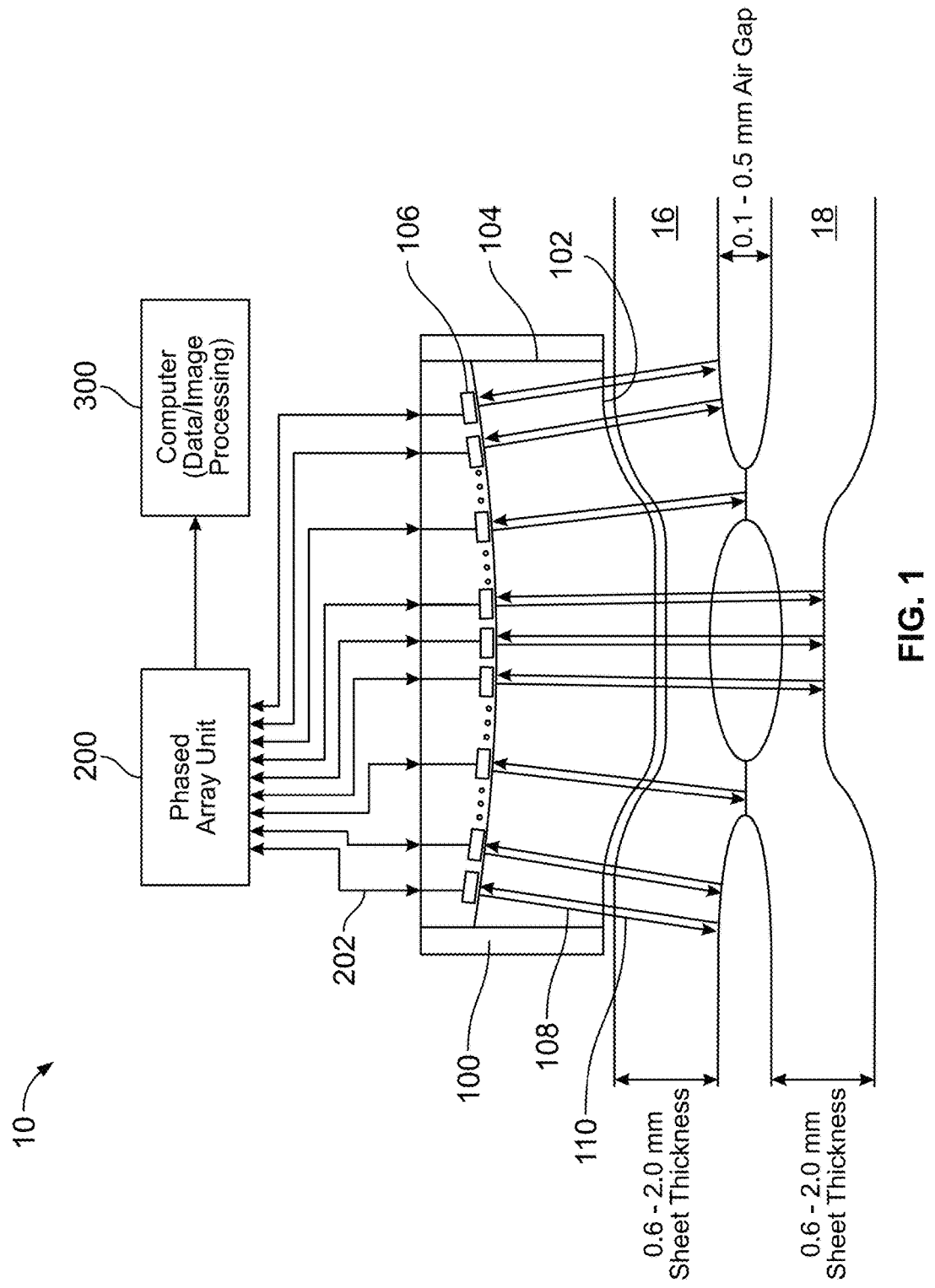
FIG. 1 is a block diagram showing the primary components of a three-dimensional matrix phased array spot weld inspection system in accordance with an exemplary embodiment of the present invention.

Exemplary embodiments of the present invention are now described with reference to the Figures. Reference numerals are used throughout the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present application incorporates by reference herein U.S. patent application Ser. No. 12/186,047, in its entirety for all purposes. With regard to the nomenclature used herein, the present invention is described as being useful for analyzing the integrity of a resistance spot weld between a first and second workpiece or upper and lower sheets of metal. However, this invention is applicable to all welds regardless of material, configuration, or the number of workpieces, as well as adhesive bonds. Thus, while the present disclosure generally refers to a stuck weld, one skilled in the art will appreciate that the present invention detects stuck portions of joints; which are often referred to as kissing bonds or weak bonds in the field of adhesives. This invention is also applicable to metals and nonmetals alike and is not limited to fusion welding, but may also be used to examine solid state welds, brazed and soldered joints. Thus, while this method has particular application in the automated analysis of spot welds, it may also be used to evaluate continuous bonds.

A stuck weld or stuck joint occurs when workpieces (e.g., pieces of sheet metal) are held together by localized fusion at the welding interface, but no weld button or weld nugget has formed as a result of the welding process. A stuck weld typically results from heat at the welding interface being insufficient to create nugget growth. In the absence of a properly formed weld nugget, fusion may occur at certain points of contact between the sheets of metal. With coated materials, coatings can melt and refreeze, effectively soldering the parts together. The resulting bonds are often strong enough to hold the workpieces together under light loads, but reasonable force will pull them apart. If ultrasonic testing is used to analyze weld integrity, transmitted ultrasonic beams (i.e., sound waves) will not pass through the interface between sheets if no fusion has occurred. If a stuck weld as occurred, resulting in fusion, but no weld nugget, transmitted ultrasonic beams will pass partially though the sheet interface. If a weld nugget has been properly formed, transmitted ultrasonic beams will pass completely through the sheet interface.

Phased Array Ultrasonic Testing (PAUT) may be used for flaw detection, sizing, and imaging. PAUT technology is the ability to modify electronically the acoustic probe characteristics. Probe modifications are performed by introducing time shifts in the signals sent to (pulse) and received from (echo) individual elements of an array probe. Three common formats for collecting and displaying ultrasonic data for purposes of non-destructive evaluation are A-scan, B-scan and C-scan presentations. Each presentation mode provides a means for visualizing and evaluating the region of material being inspected. An A-scan is a simple RF waveform presentation showing the time and amplitude of an ultrasonic signal, as commonly provided by conventional ultrasonic flaw detectors and waveform display thickness gages. A-scan is an amplitude modulation scan, and as generally applied to pulse echo ultrasonics, horizontal and vertical sweeps are proportional to time or distance and amplitude or magnitude respectively. Thus the location and magnitude of acoustical interface are indicated as to depth below the transducer. The relative amount of energy received is plotted along the vertical axis and the elapsed time (which may be related to the sound energy travel time within the material) is displayed along the horizontal axis. Most instruments utilizing an A-scan display allow the signal to be displayed in its natural radio frequency form (RF) as a fully rectified RF signal or as either the positive or negative half of the RF signal. In the A-scan presentation, relative discontinuity size can be estimated by comparing the signal amplitude obtained from an unknown reflector to that from a known reflector. Reflector depth can be determined by the position of the signal on the horizontal sweep. A C-scan from a phased array system involves an ultrasonic probe being physically moved along one axis while the beam electronically scans along the other axis according to the focal law sequence. Signal amplitude or depth data is collected within gated regions of interest. Data is plotted with each focal law progression, using the programmed beam aperture. Utilizing a matrix phased array probe, beam steering can be accomplished in multiple directions.

With reference to the Figures, an exemplary embodiment of the present invention provides a nondestructive inspection system for assessing the quality of resistance spot welds. As shown in FIG. 1, which is a block diagram of an exemplary embodiment, spot weld inspection system 10, is operative to assess the quality of weld 12, which is formed at interface 14, which is located between upper sheet 16 and lower sheet 18 (both having a sheet thickness of about 0.6 mm to about 2.0 mm). An air gap of about 0.1 mm to about 0.5 mm may be present between upper sheet 16 and lower sheet 18. A three-dimensional, matrix phased array probe 100 is placed on the region of upper sheet 16 that is located over the welded area. A curved array of ultrasonic elements 106 is used to transmit a plurality of ultrasonic beams 108 into the welded area and to capture the associated reflections 110 of those ultrasonic beams. Phased array unit 200 is in electrical communication with the plurality of ultrasonic elements 102 through a plurality of signal pathways 202. Phased array unit 200 is also in electrical communication with computer 300, which processes incoming ultrasonic data and generates a visual representation of the welded area. Probe 100 includes flexible membrane 102, which allows the tip of the probe to conform to the contour of the welded area and fluid filled chamber 104 or solid sound delay material for focusing and steering ultrasonic beams 108. Because flexible membrane 102 is capable of conforming to curved surfaces as shown in FIG. 1, and because the array of transducer elements 106 is configured in a curved geometry (see FIG. 1), the matrix phased array system of this invention is referred to as "three-dimensional" as opposed a "two-dimensional" system which uses a probe having a flattened array and a flat tip.

Figure 2A:
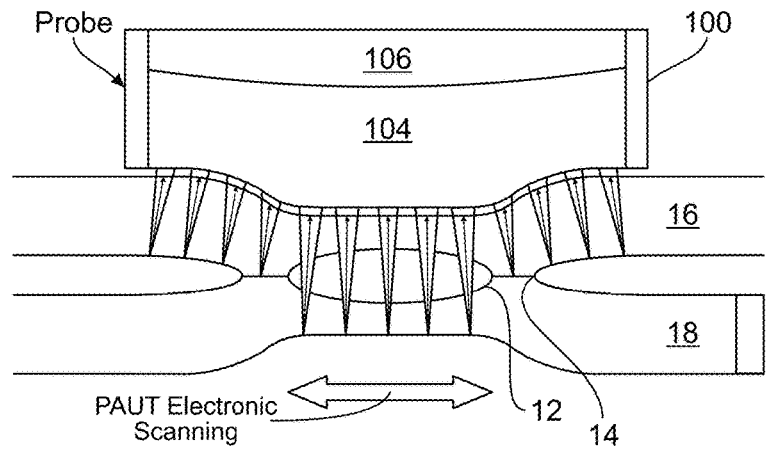
FIGS. 2a-c provide illustrations of test results derived from analyzing a good spot weld using the system of FIG. 1.
Figure 2B:
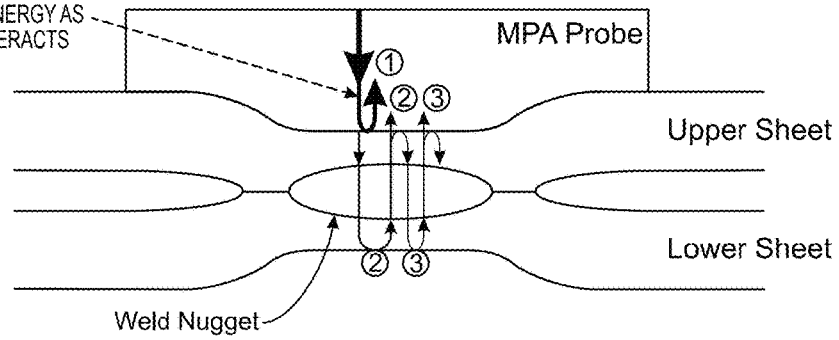
Figure 2C:
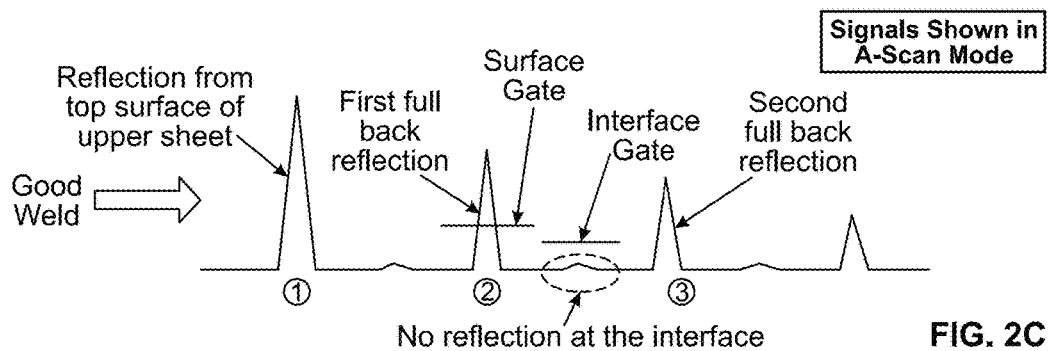
Figure 3:
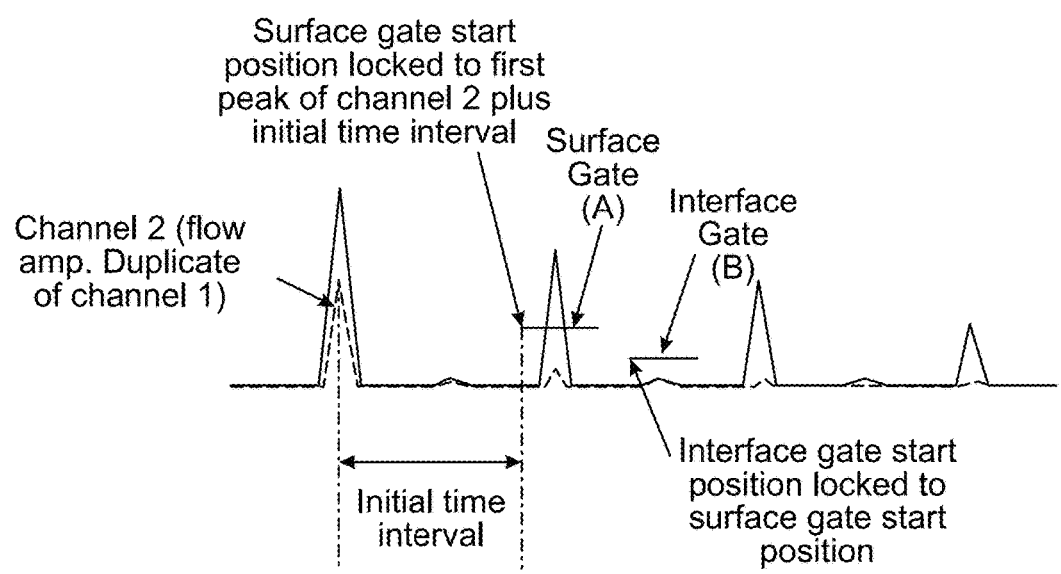
FIG. 3 provides a visual representation in A-scan mode of the electronic gates included in the weld inspection system of FIG. 1.

FIGS. 2a-c provide illustrations of test results derived from analyzing a good spot weld using system 10. In FIG. 2a, ultrasonic beams travel completely through weld 12 and interface 14 and reflect back to probe 100 from the backside of lower sheet 18. FIG. 2b illustrates diagrammatically the direction and relative strength of each sound wave as it transmits and reflects at interface 14. In FIG. 2b, a thinner line represents loss of acoustic energy as the sound wave interacts with interface 14. The reflected signals designated as circled 1, and 3 correspond to the peaks shown in the A-scan presented in FIG. 2c. FIG. 2c provides the signals derived from testing in A-scan mode, wherein signal 1 represents the reflection from the top surface of upper sheet 16, signal 2 represents the first full back reflection, and signal 3 represents the second full back reflection. The horizontal line drawn through signal 2 represents a surface gate and the horizontal line adjacent to signal 2 represents an interface gate (see discussion below.)

Based on the ultrasonic energy transmission and reflection at weld interface 14 and the back side of lower sheet 18, system 10 uses two adjustable electronic gates to filter out all unwanted reflected signals. The two signals that pass through the gates are either the reflected signal from the back side of the second sheet of metal or the reflected signal from the interface of the two sheet metals. The first gate is called the "surface gate" and the second gate is called the "interface gate". This approach differs from the current commercially available systems that utilize an attenuation coefficient compensation method. In such systems, multiple reflections from all of surfaces and the interface are taken into account to determine attenuation coefficients and make a correction for acoustic energy loss caused by the spot weld fusion, assuming that the microstructure of fused section of the spot weld has a higher attenuation coefficient compared to a stuck weld condition. As disclosed and claimed in U.S. patent application Ser. No. 12/186,047, which is incorporated by reference herein, each ultrasonic element in array 106 generates a primary ultrasonic beam and a secondary ultrasonic beam wherein the primary ultrasonic beam is high gain and wherein the secondary ultrasonic beam is low gain; and wherein the primary and secondary ultrasonic beams are fired in within very close proximity to one another i.e., milliseconds). As shown in FIG. 4, channel 2 is a low amplitude duplicate of channel 1 in each peak. The initial time interval shown is measured from the center of the first peak to the surface gate start position. The surface gate start position is locked to the first peak of channel 2 plus the initial time interval. The interface gate start position is locked to the surface gate start position. System 10 measures the ration of signal amplitude (height) between gate A and B and only signals between the gate start and end positions are considered.

Figure 4A:
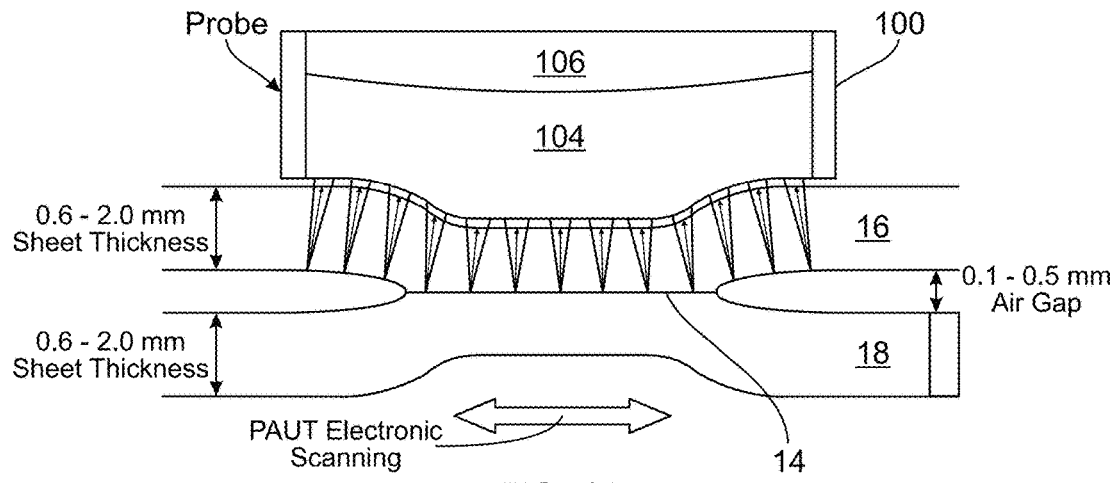
FIGS. 4a-c provide illustrations of test results derived from analyzing a poor spot weld using the system of FIG. 1.
Figure 4B:
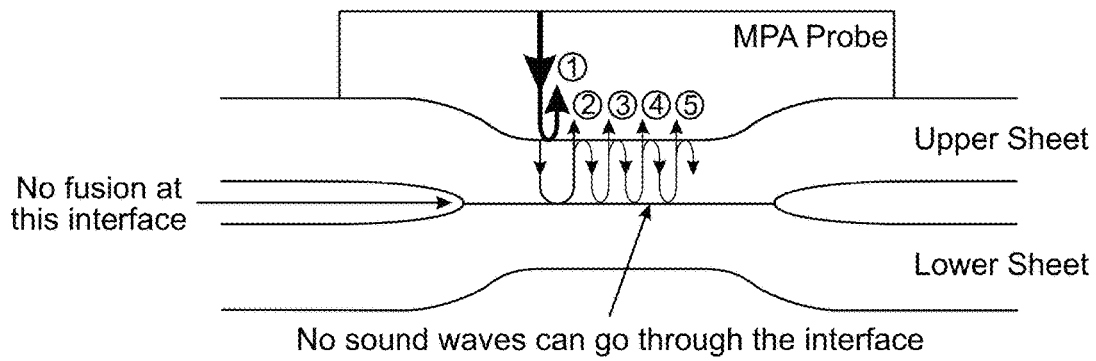
Figure 4C:
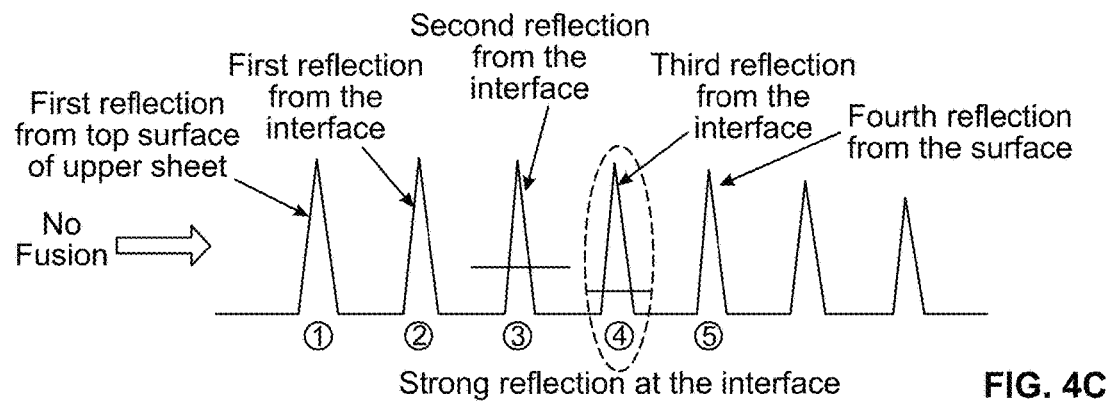

FIGS. 4a-c provide illustrations of test results derived from analyzing a poor spot weld using system 10. In FIG. 4a, because no weld nugget exists, ultrasonic beams do not travel completely through interface 14, hut rather reflect back to probe 100 from interface 14. FIG. 4h illustrates diagrammatically the direction and relative strength of each sound wave as it reflects at interface 14. In FIG. 4b, a thinner line represents loss of acoustic energy as the sound wave interacts with interface 14. The reflected signals designated as circled 1, 2, 3, 4, and 5 correspond to the peaks shown in the A-scan presented in FIG. 4c. FIG. 4c provides the signals derived from testing in A-scan mode, wherein signal 1 represents the first reflection from the top surface of upper sheet 16, signal 2 represents the first reflection from interface 14, signal 3 represents the second reflection from interface 14, signal 4 represents the third reflection from interface 14, and signal 5 represents the fourth reflection from interface 14. The horizontal line drawn through signal 3 represents the surface gate and the horizontal line drawn though signal 4 represents the interface gate (see discussion above.)

Figure 5A:
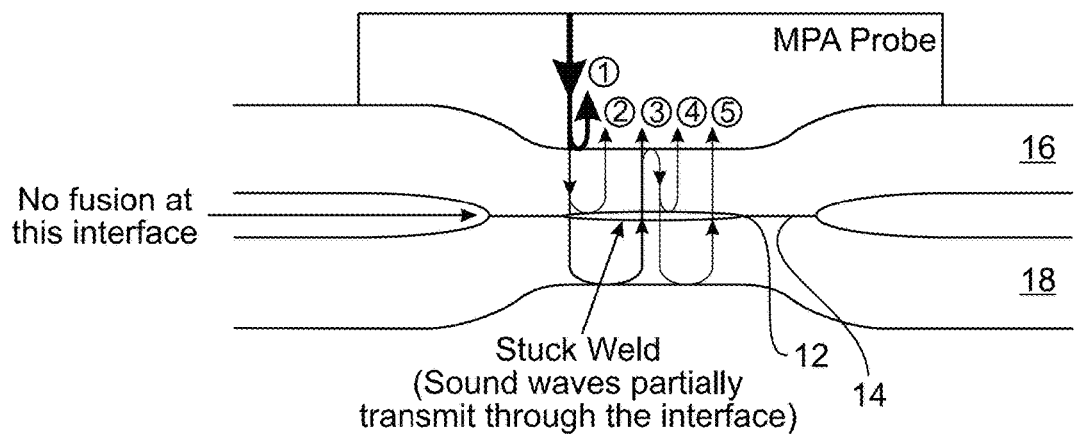
FIGS. 5a-b provide illustrations of test results derived from analyzing a stuck weld using the system of FIG. 1.
Figure 5B:
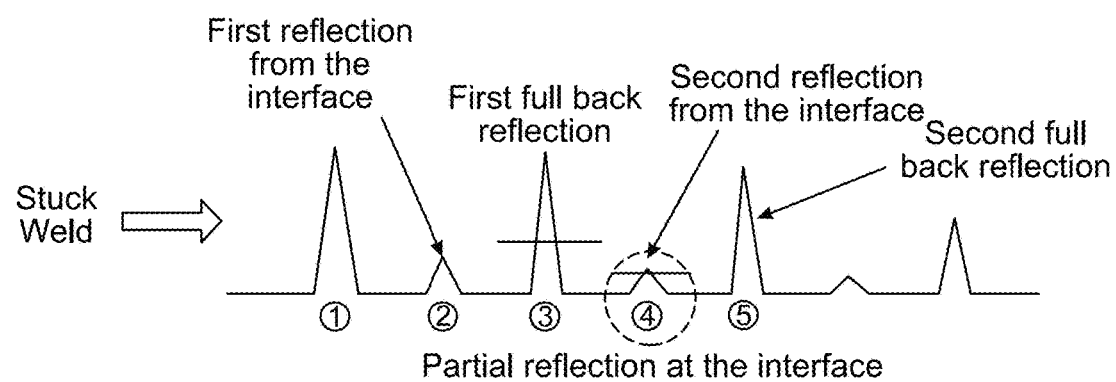

FIGS. 5a-b provide illustrations of test results derived from analyzing a stuck weld using system 10. Because an incomplete or poorly formed weld exists, ultrasonic beams travel only partially through interface 14, while intermediate echoes appear between the echoes of interface 14 and fill back wall reflection. FIG. 5a illustrates diagrammatically the direction and relative strength of each sound wave as it transmits and reflects at interface 14. In FIG. 5a, a thinner line represents loss of acoustic energy as the sound wave interacts with interface 14. The reflected signals designated as circled 1, 2, 3, 4, and 5 correspond to the peaks shown in the A-scan presented in FIG. 5b, FIG. 5b provides the signals derived from testing in A-scan mode, wherein signal 2 represents the first reflection from interface 14, signal 3 represents the first full back reflection, signal 4 represents the second reflection from interface 14, and signal 5 represents the second full back reflection. The horizontal line drawn through signal 3 represents the surface gate and the horizontal line drawn though signal 4 represents the interface gate (see discussion above.)

Figure 6A:
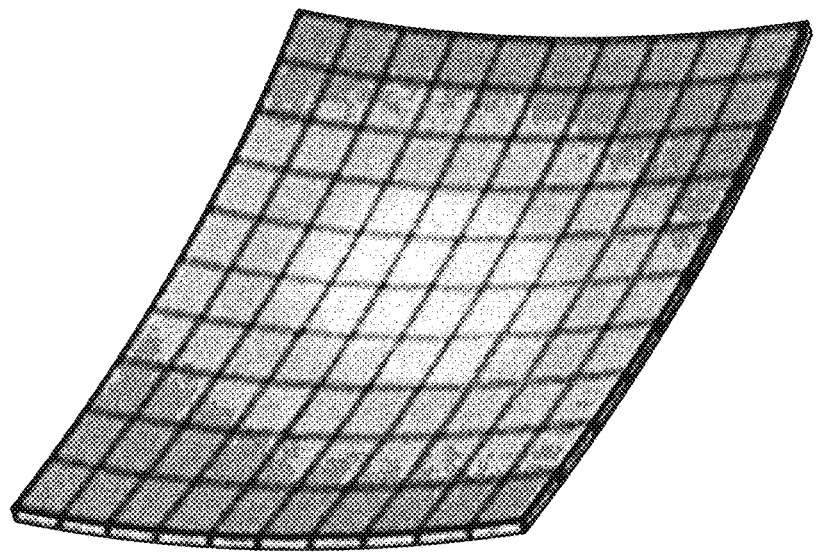
FIGS. 6a-b illustrate the shape of the 3-D curved probe element as well as various firing sequences for the sub-element groups.
Figure 6B:
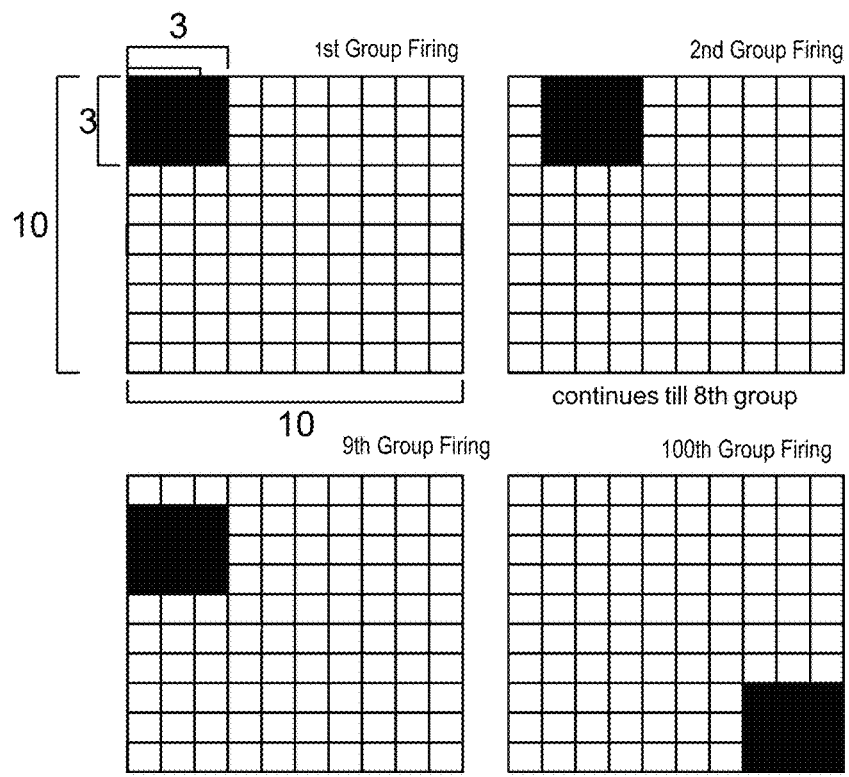

FIGS. 6a-b illustrate the geometry of the curved three-dimensional probe element (FIG. 6a) as well as various firing sequences for the sub-element groups (FIG. 6b). Acoustic probe 100 includes a plurality of ultrasonic transducer elements 106 arranged in a three-dimensional array and having a combination of materials for allowing the probe to conform to the contoured surface of a spot weld while enabling the sound energy to be transferred directly into the spot weld under test. An excitation element (phased array unit 200) is coupled to the array and a subset group of transducer elements are combined to send an ultrasonic beam toward a spot weld. Each transducer element in a subset group may be pulsed at different time intervals (phase delay) and their individual waves summed to produce a focusing effect of the beam as well as a steering effect. Other three-dimensional arrangements are possible for optimizing the performance for specific applications. The total number of elements, overall dimension, and operating frequency determine the overall three-dimensional surface contour shape and its operating characteristics and parameters.

Figure 7A:
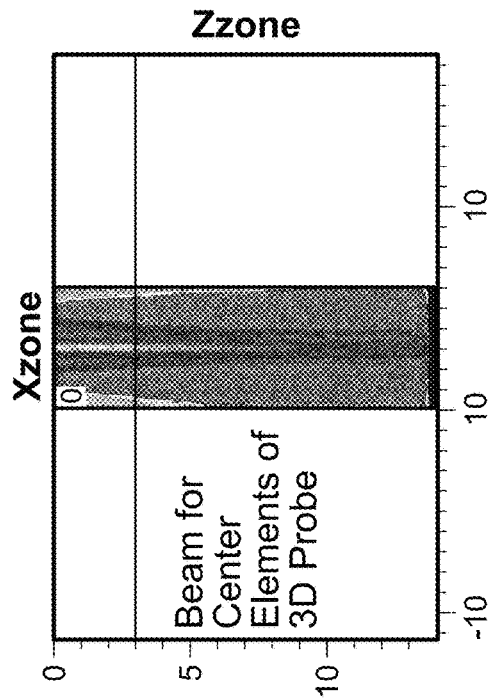
FIGS. 7a-d provide modeling verification of the benefits of a 3-D curved probe design versus a 2-D flat probe design.
Figure 7B:
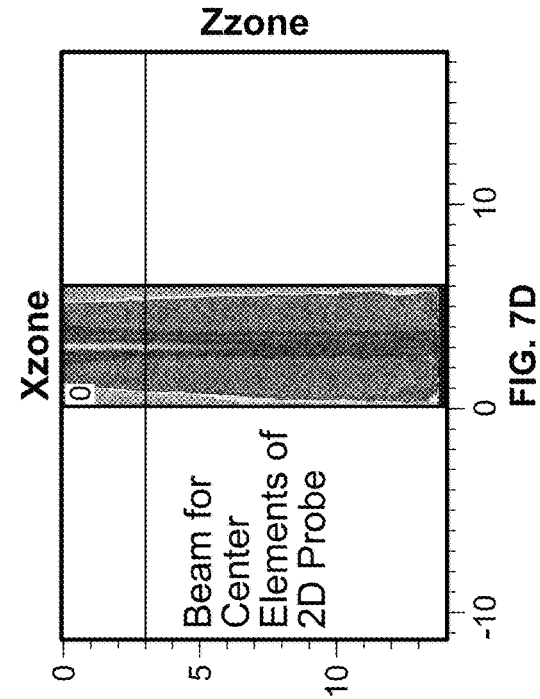
Figure 7C:
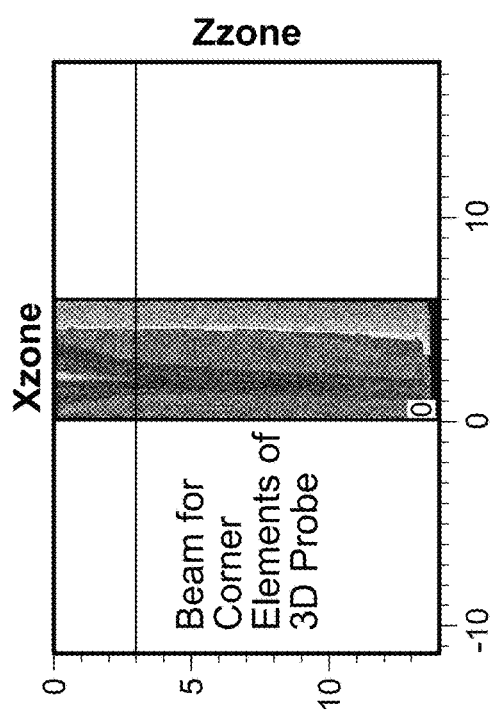
Figure 7D:
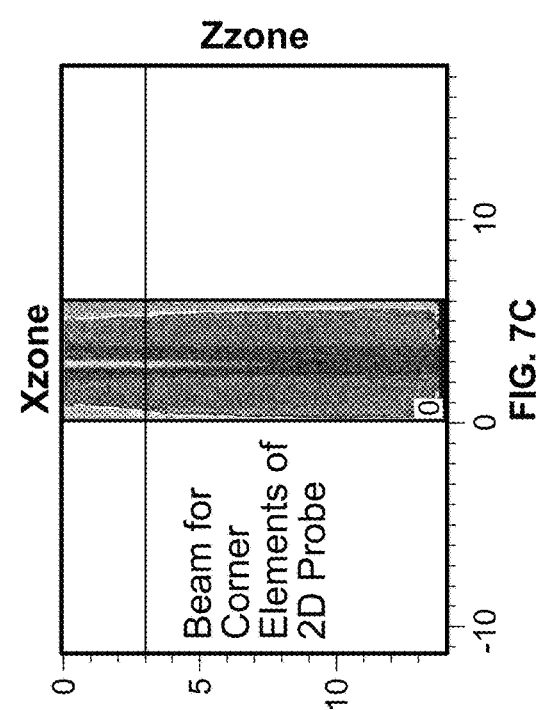

The design of the three-dimensional probe permits inspection of a larger physical area with a smaller probe, thereby allowing for improved probe access as well as a wider coverage area compared to two-dimensional designs. The three-dimensional geometrical arrangement provides optimized accuracy and sensitivity in particular regions of the weld joint. As illustrated by FIGS. 7a-d, the result of corner elements of the three-dimensional curved probe shown in FIG. 7a illustrates that the beam launch angle is more steered to the normal direction of the typical spot weld indentation when compared to the two-dimensional flat probe case shown in FIG. 7c. There is no noticeable change in the beam quality for the center elements for both three-dimensional (FIG. 7b) and two-dimensional (FIG. 7d) probes. Without losing the fidelity of inspection capability with the two-dimensional matrix phased array probe, the three-dimensional probe extends the coverage area from the built-in curvature of the probe itself. This invention therefore allows inspection of a larger weld area with a smaller probe diameter, allowing improved access. It may also allow use of fewer numbers of elements, reducing overall system cost, while still covering the entire weld area.

Figure 8:
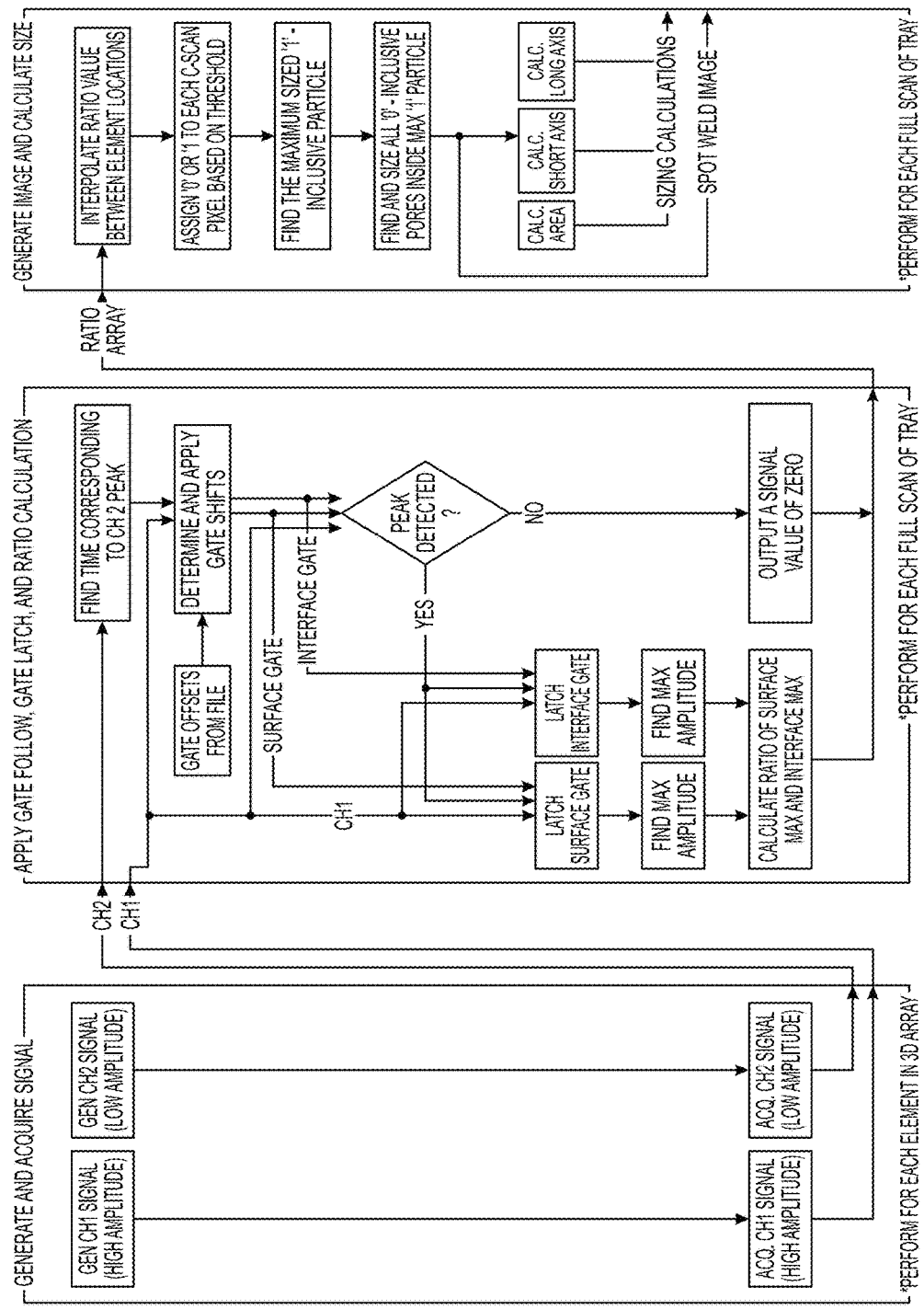
FIG. 8 provides a data flow chart for an exemplary embodiment of the spot weld inspection process of the present invention.
Figure 9:
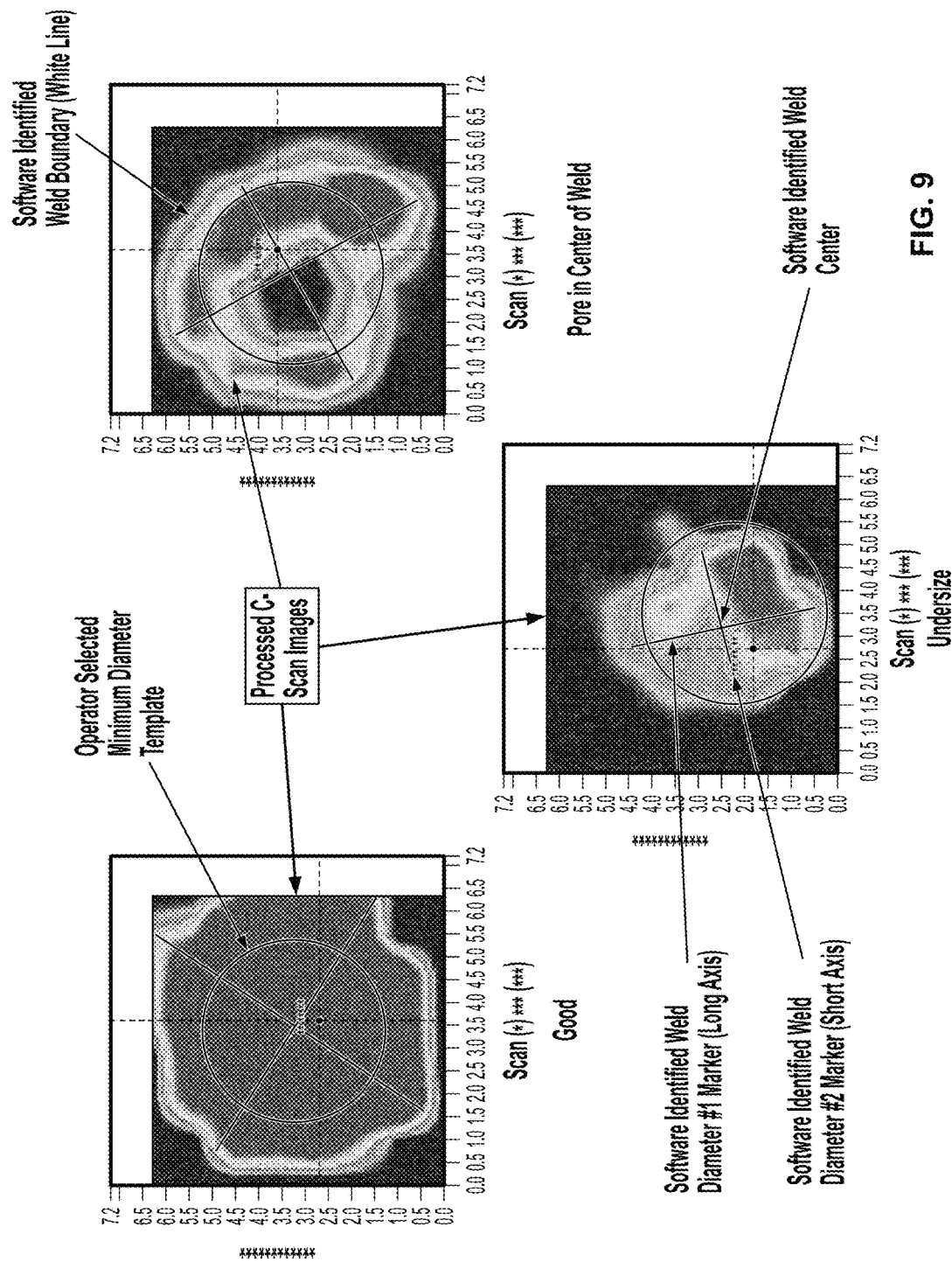
FIG. 9 provides examples of imaging results for various spot weld conditions.

In various embodiments of this invention, a computerized controller is coupled to acoustic probe 100 and transducer elements 106 for directing transmission of the ultrasonic signals and for summing and receiving responses therefrom. With general reference to FIG. 8 (which provides a flowchart that illustrates the function of one possible operating system), the controller is operative to (i) generate and acquire acoustic signals; (ii) detect the surface of the spot weld for each element grouping; (iii) adjust instrument gating to compensate for surface profile and differences in probe orientation; (iv) measure the signal amplitude ratio between responses reflected from the un-bonded areas and areas with good bond; (v) recognize a subset of the responses as being reflected from the un-bonded areas associated with the spot weld and to separate the subset from a remainder of the responses; (vi) measure the extent of the non-delamination dimensions; and (vii) present a two-dimensional color coded image of non-delamination of the spot weld (see FIG. 9). In summary, some of the distinct advantages of this invention include: (i) a three-dimensional matrix probe element; (ii) a phase delay with sub-element group to form a beam focusing and steering capability; (iii) conformable membrane (no need for an attenuation correction); and (iv) an image process utilizing electronic gates to filter out unwanted reflections.

An important aspect of the present invention is a technique for translating A-scan signals into a quality map of the sensing field of view using an algorithm specific to the technique. Continual evolution of the present invention and testing of the inspection system in industrial environments has yielded certain advancements to the algorithm. Specifically, these advancements improve the accuracy and robustness of the quality evaluation and provide a more streamlined experience for the user. These advancements can be grouped into the following categories: (i) Gate Ratio; (ii) Gate Following; (iii) Gate Latching; (iv) Alignment Feedback. The algorithm describes the process of ultrasonically scanning a weld using phased-array principles and using the generated data, in the form of A-scans, to create or "paint" an image of weld fusion across the sensor's field of view and to calculate fusion measurements from this image.

Figure 10:
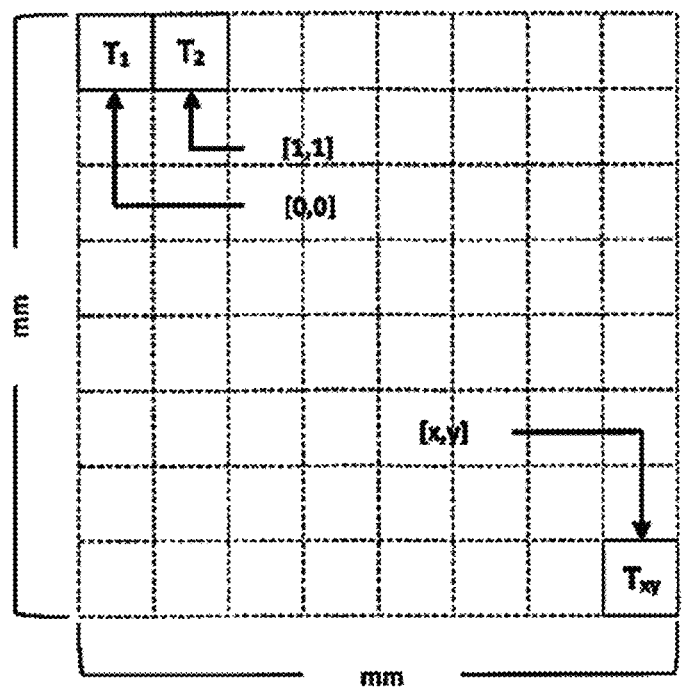
FIG. 10 provides a schematic of focal law index breakdown with respect to location within the sensor field of view.

A first step (Step 1) involves generating the data, which is done by controlling a multitude of transmissions across the field of view of a matrix phased-array sensor. The number of transmissions can vary and the number of elements which are included in each transmission can vary, but the important point is that each transmission interrogates a different portion of the sensor's field of view. FIG. 10 illustrates this concept where transmission 1 ($T_1$) describes the material under index (0,0); transmission 2 ($T_2$) describes the material under (0,1); and so on to index (x,y). Executing a full set of transmissions through the entire field of view constitutes a sequence. The result is a set of A-scans that includes analog data describing how the ultrasound is transmitted and reflected for each position within the sensor's field of view.

Figure 11:
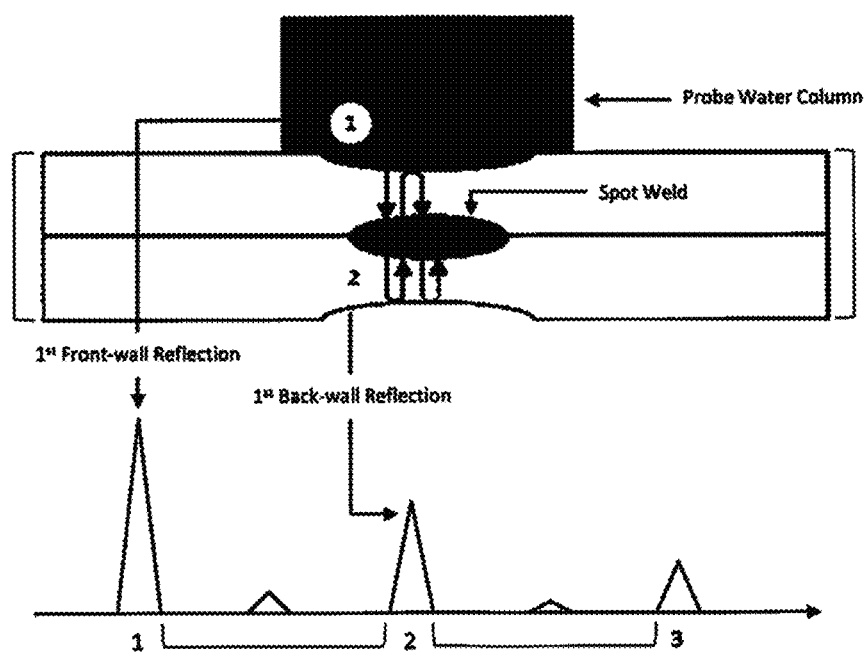
FIG. 11 provides a schematic of ultrasound reflections with representative a-scan output.

A second step (Step 2) involves interrogation of these A-scans with the objective of producing a fusion indication metric for each position within the field of view. This is done by examining the A-scan data within a region of interest, specifically the range of data representing the stackup thickness. FIG. 11 provides a schematic depicting how the ultrasound traverses and reflects through the material. The span along the A-scan between the front-wall and back-wall reflections is the key area for investigation. It is within this span that the weld resides and therefore it is within this span that the inspection is focused, FIG. 12 illustrates two scenarios, (1) where the ultrasound goes through the weld and reflects off of the back-wall; and (2) where the ultrasound reflects off of the sheet-to-sheet interface.

Figures 12, 13:
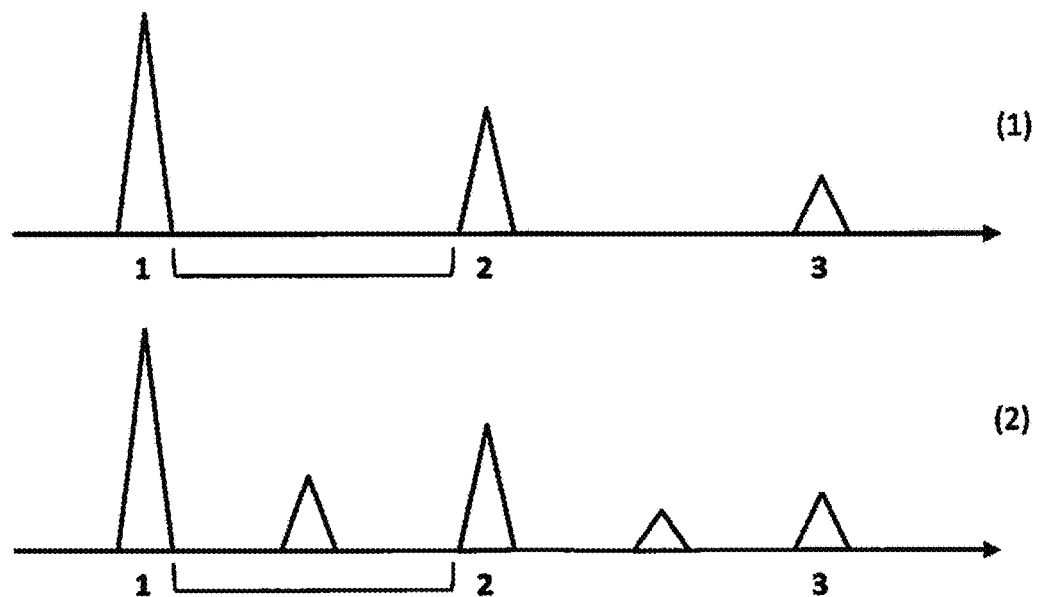
FIG. 12 provides fused (1) and unfused (2) A-scan representations.
FIG. 13 provides a graphical representation of an exemplary fusion metric, wherein the letters "a" represent a region of the metric furthest from a target area of the metric, wherein the letters "b" represent a region closer to the target area of the metric, and wherein the letters "c" represent the target area of the metric.

The fusion metric has been previously described as being a one-to-one inverse correlation to the maximum amplitude detected within the full thickness of the stackup (represented by brackets in FIG. 12). No fusion is represented by full-scale amplitude (maximum amplitude detectable by the ultrasonic system). Full fusion is represented by full-scale minimum (zero for rectified signal). The fusion metrics are then plotted graphically on either a monochrome or color scale (matching full-scale of the A-scan data) by their position within the field of view. FIG. 13 illustrates an idealized example representation of the fusion metric plotted along the field of view for a circular spot weld. In the center of the field of view, the A-scans exhibit no reflection and thus a high metric. In the periphery of the field of view A-scans exhibit a reflection from the unfused metal and thus a low metric.

A third step (Step 3) utilizes the graphical fusion representation for measuring fusion characteristics. Specifically, the area of fusion and the diameter of fusion are measured for spot weld applications. This is done by first empirically determining a threshold fusion metric that differentiates 'good' fusion from 'bad' fusion. With this threshold defined, the resultant fusion image (see FIG. 13) can be interrogated. For spot welding, the weld is determined by finding the largest continuous agglomeration of 'good' fusion data points and drawing a perimeter around it. The area of the spot weld is simply the area within this agglomeration (pixels translated into engineering units), minus any donut holes of unfused area. The diameter is measured by walking around the perimeter of the agglomeration to find largest diameter and shortest diameter (2 points are 180 degrees apart). These aspects of the present invention permit: (a) more accurate results; (b) more robust results across a range of applications and noise factors; and (c) providing the user with feedback regarding inspection performance. Each of these aspects is described in greater detail below.

Figure 14:
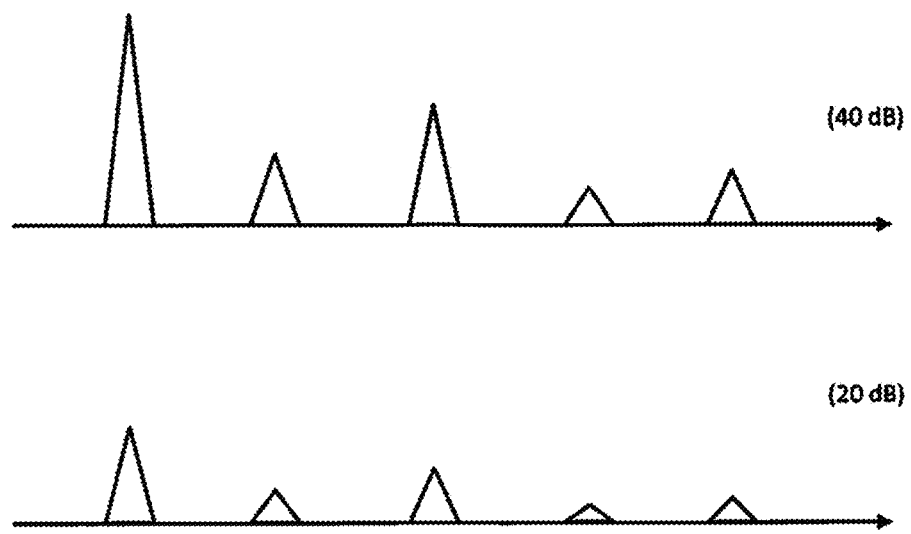
FIG. 14 graphically s the effect of gain variation on A-scan magnitudes.
Figure 15:
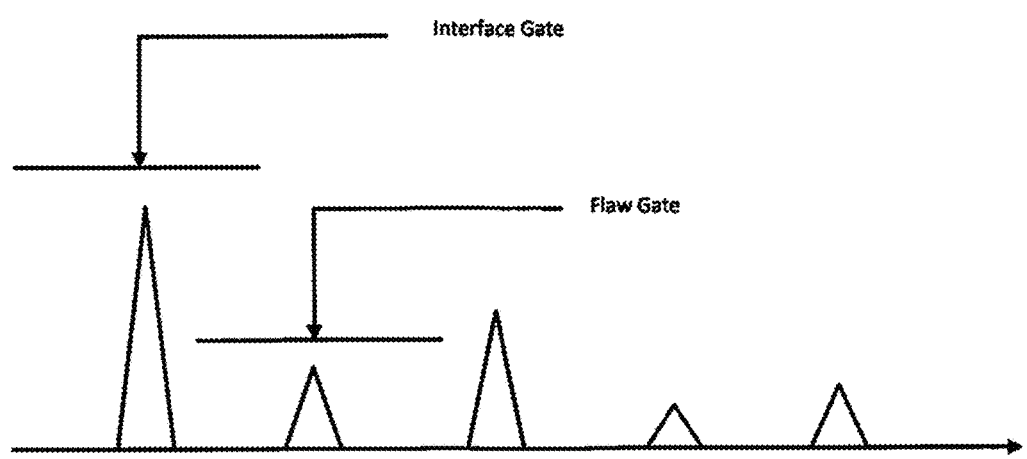
FIG. 15 provides a schematic of gate ratio gate placement.

This invention includes the aspect or principal of gate ratio. A limitation of earlier embodiments of this invention is the method by which the fusion metric is calculated and evaluated. The evaluation of the fusion metric is a simple threshold comparison. If it is greater than the threshold, it constitutes 'good' fusion and if it is less than the threshold, it constitutes 'bad' fusion. The problem is this threshold value is dependent on a number of factors including gain, material, beam angle, etc. As these factors vary, the magnitude of the entire A-scan can vary. FIG. 14 illustrates this through a set of A-scans with varying gain settings. This data represents the same exact weld with different gain settings. Here, the fusion metrics result in completely different values when they should be substantially identical (i.e., the same weld is being evaluated). The limitation is due to the fusion metric being linked singularly to the maximum amplitude under the flaw gate without any link to the overall quality of the signal traversing through the weld. The "gate ratio" adds this extra level of intelligence by using the interface gate as a metric of signal quality and using it to normalize each fusion metric. Instead of taking just the maximum amplitude under the flaw gate, a ratio is taken between the maximum amplitudes under the flaw gate and the interface gate (see FIG. 15). Therefore; as signal quality is decreased or increased, the fusion metric for a given weld remains constant. This is important for usability as one universal fusion threshold can be used. Additionally, this aspect helps to make the overall fusion measurements more accurate as the divot evinced in spot welds acts as a source of variance to the signal quality. In other words, with the original algorithm the fusion threshold could be tuned for either the weld region or the periphery region; but not both. The result here is a better defined cutoff between 'good' fusion and 'bad' fusion.

Figure 16:
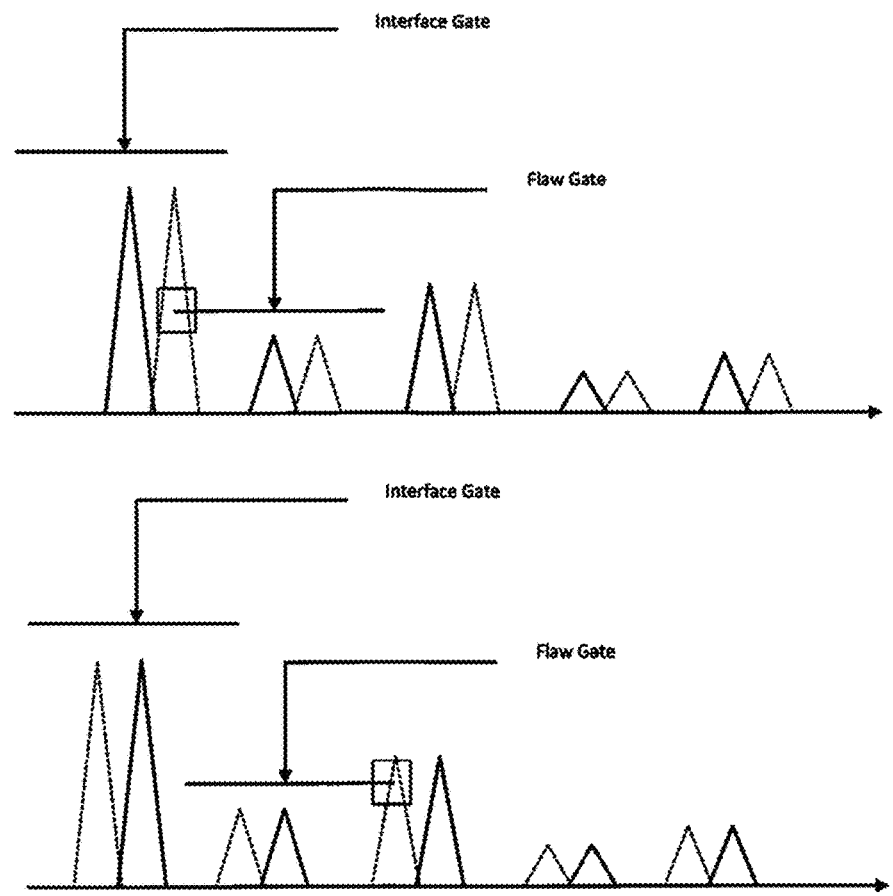
FIG. 16 graphically illustrates A-scan drift and the effect on gate output.

This invention also includes the aspect or principal of gate following. Another limitation of earlier embodiments of this invention is the absence of any gate following algorithm. A-scan data is digitized as a function of time subsequent to the pulsing event. As the standoff between the pulsing elements (i.e., the sensor) and the material interface varies (typical with manual and robotic manipulation) the signal moves in and out of the digitizing range. The gate positions, however, remain constant within the digitizing range. Accordingly, without gate following functionality, the gates may intrude into undesirable areas of the A-scan and report erroneous results. FIG. 16 illustrates example A-scans that have shifted to different positions. In each shift case, the flaw gate return is erroneous as it includes a maximum value from an unwanted signal. Circumventing this issue requires a link to be made between the gate offset and a landmark within the A-scan signal for purposes of gate following. This is achieved by using the first front-wall interface signal as a means for tracking. A gate is placed across the full span of the A-scan to find the greatest amplitude. If the alignment of the probe is good, this will always return the position of the first front-wall interface signal peak. As this peak position shifts from a nominal ($\Delta t$) the same shift is applied to both gate offsets. This keeps the gates properly aligned with the A-scan signal. The result is an algorithm with a greater degree of robustness to deal with real world variation.

Figure 17:
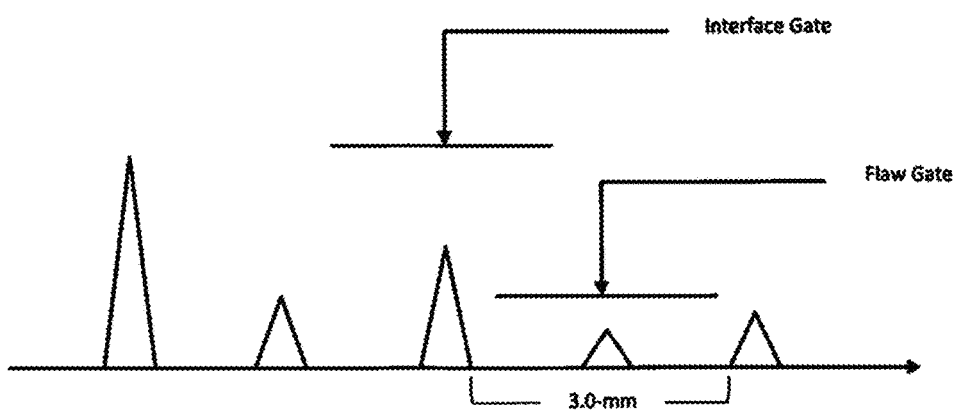
FIG. 17 graphically illustrates the initial set up of a 0.6×1.2×1.2-mm stackup.
Figure 18:
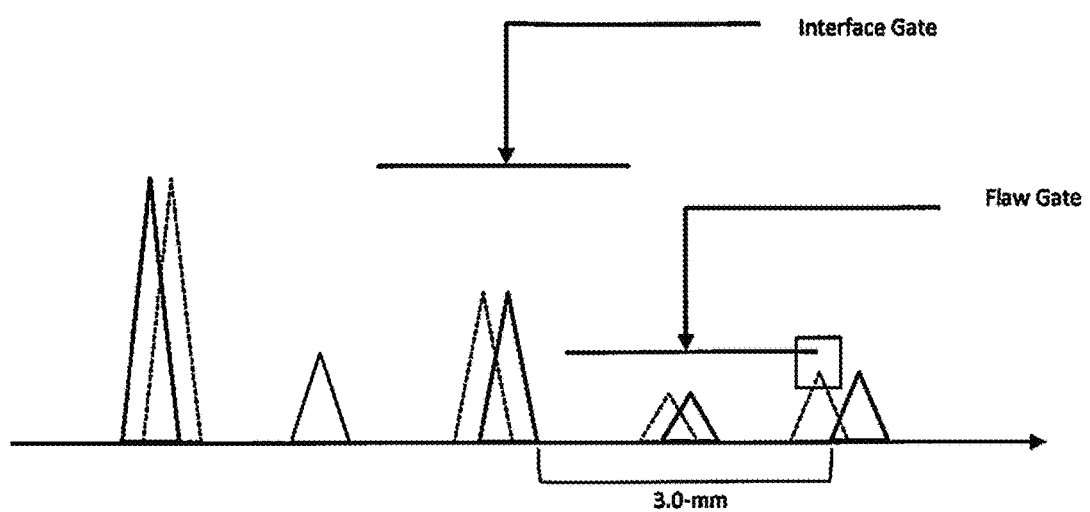
FIG. 18 provides an A-scan shift representation with varying deformation divots.

This invention also includes the aspect or principal of gate latching. In addition to A-scan drifting, real world application of earlier-used algorithms discovered that not all stackups are created equal. A stackup is defined as the set of material thicknesses and material types in which a weld is produced. For example, a stackup may be three ply, all mild steel, with thickness of 0.6-mm, 1.2-mm, and 1.2-mm, from top to bottom. The total thickness would be 3.0-mm. Set up of the algorithm requires the initial placement of interface and flaw gates as illustrated in FIG. 17. This will be done on one representative 0.6×1.2×1.2-mm weld and applied to all other 0.6×1.2×1.2-mm welds. This is not an issue as long as all 0.6×1.2×1.2-mm stackups are produced in a similar fashion and manifest similar deformation during welding. However, in practice no two spot welds are identical. To some degree, each receives variant force, current, duration, etc., and may deform differently. If a spot weld divot is greater than the one which was used for set up, the gates, again, may intrude into undesirable regions of the A-scan and produce erroneous results. For example, FIG. 18 illustrates the shift of an A-scan with the same stackup details as FIG. 17, but a larger deformation divot. What occurs is the inclusion of high amplitudes from either a front-wall or back-wall reflection into the expected flaw gate region.

Circumventing the above issue requires a link between divot deformation and gate offset and length to dynamically latch the flaw gate into proper position. This is applied in practice by first determining the position of the interface gate maximum amplitude with respect to the gate offset and length. What is determined is how well the position of the interface gate maximum amplitude is centered under the interface gate. If the maximum amplitude is shifted towards the start of the interface gate this means the deformation is greater (assuming interface gate on backwall) than expected. The algorithm then snaps or latches the flaw gate towards the interface gate and reduces the flaw gate length. If the maximum amplitude is shifted away from the start of the interface gate this means the deformation is less (assuming interface gate on backwall) than expected. The algorithm then snaps or latches the flaw gate away from the interface gate and increases the length. This algorithm keeps the flaw gate positioned properly within the flaw region and maximizes the size of the gate for optimal flaw detection.

Figure 19:
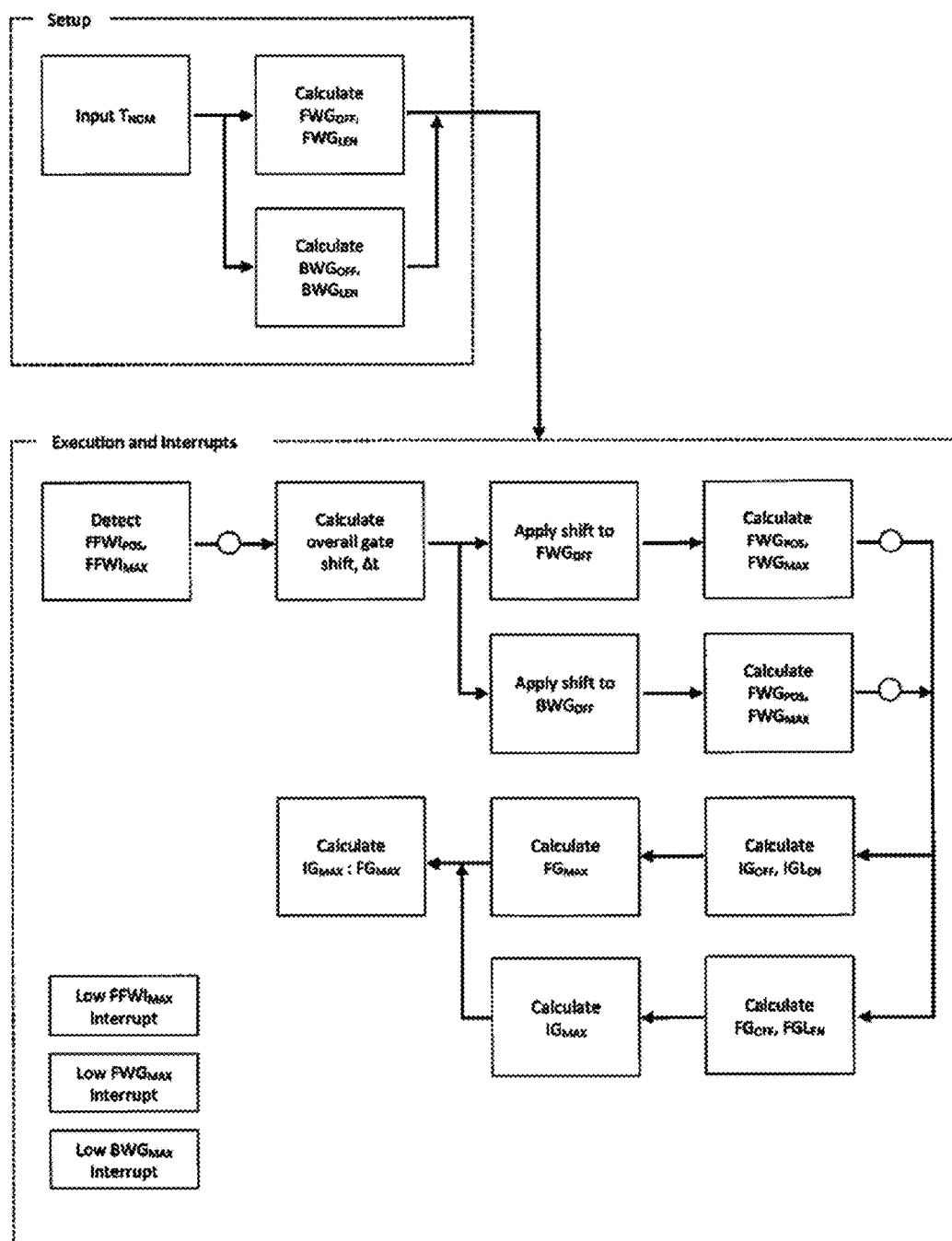
FIG. 19 provides a flow chart of the dynamic gating algorithm of the present invention.

Current operation of the described system for ultrasonically characterizing weld fusion determines the placement and length of interface and flaw gates. Significant logic has been implemented within the system algorithm to manage the proper placement of the interface and flaw gates. The algorithm described below uses a unique perspective on the placement of these gates by focusing first on finding the front-wall and back-wall positions and then placing the gates according to these determinations. With reference to FIG. 19, an exemplary algorithm flows as follows:

Setup (1) The total stackup thickness is known, $T_{NOM}$
(2) A nominal front-wall interface gate is automatically set by centering it at the expected position ($FWG_{OFF}$) with a length of $0.75T_{NOM}$ ($FWG_{LEN}$)
(3) A nominal back-wall interface gate is automatically set by centering it at the expected position ($BWG_{OFF}$) with a length of $0.75T_{NOM}$ ($BWG_{LEN}$)

Execution (1) A gate is applied across the full range of the digitized A-scan to detect the first front-wall interface, $FFWI_{POS}$ and $FFWI_{MAX}$
(2) A differential between the expected $FFWI_{POS}$ and the actual $FFWI_{POS}$ is calculated, $\Delta t$
(3) The front-wall and back-wall interface gates are adjusted by the $\Delta t$
$FWG_{OFF}+\Delta t$
$BWG_{OFF}+\Delta t$
(4) Position of FWG maximum amplitude is found, $FWG_{POS}$ and $FWG_{MAX}$
(5) Position of BWG maximum amplitude is found, $BWG_{POS}$ and $BWG_{MAX}$
(6) Offset and length of the interface gate are calculated, $IG_{OFF}$ and $IG_{LEN}$
    Centered on either the position of $FWG_{MAX}$ or $BWG_{MAX}$ (user-selectable)
    Gate length is calculated as a percentage of length between the positions for $FWG_{MAX}$ and $BWG_{MAX}$
(7) Offset and length of the flaw gate are calculated, $FG_{OFF}$ and $FG_{LEN}$
    Centered between the positions of $FWG_{MAX}$ or $BWG_{MAX}$
    Gate length is calculated as a percentage of length between the positions for $FWG_{MAX}$ and $BMG_{MAX}$
(8) Maximum amplitude under the IG is found, $IG_{MAX}$
(9) Maximum amplitude under the FG is found, $FG_{MAX}$
(10) Ratio between $IG_{MAX}$ and $FG_{MAX}$ is calculated Interrupts (1) The $FFWI_{MAX}$ must be greater than a threshold value, otherwise the ratio is 0
(2) The $FWG_{MAX}$ must be a certain percentage greater than the average amplitude under the gate (a) Otherwise the ratio is 0 if the front-wall is being used as the interface gate
(b) Otherwise the IG and FG length is assumed if the front-wall is not being used as the interface gate
(3) The $BWG_{MAX}$ must be a certain percentage greater than the average amplitude under the gate
(a) Otherwise the ratio is 0 if the back-wall is being used as the interface gate
(b) Otherwise the IG and FG length is assumed if the back-wall is not being used as the interface gate This invention may also provide alignment feedback. Alignment of the probe, whether manually or robotically manipulated, is crucial to obtaining proper signal strength and beam orientation through the weld. Therefore, some means of feedback is important for providing an operator or robot controller with the means to properly adjust. As mentioned in the gate following algorithm above, it has been observed that the interface signal is a good indication of signal strength. The goal is to maximize the signal strength through the center of the field of view, therefore, the interface signals of the center A-scans can be used as a means of feedback. For the center portion of the field of view, each A-scan is interrogated to find the maximum amplitude associated with first front-wall interface. The greater this amplitude, the better the probe alignment is with the weld axis. This alignment metric may be fed back to the operator through a graphical or numerical representation. Additionally, the alignment metric can be fed to a robot controller for adjustment.

Figure 20:
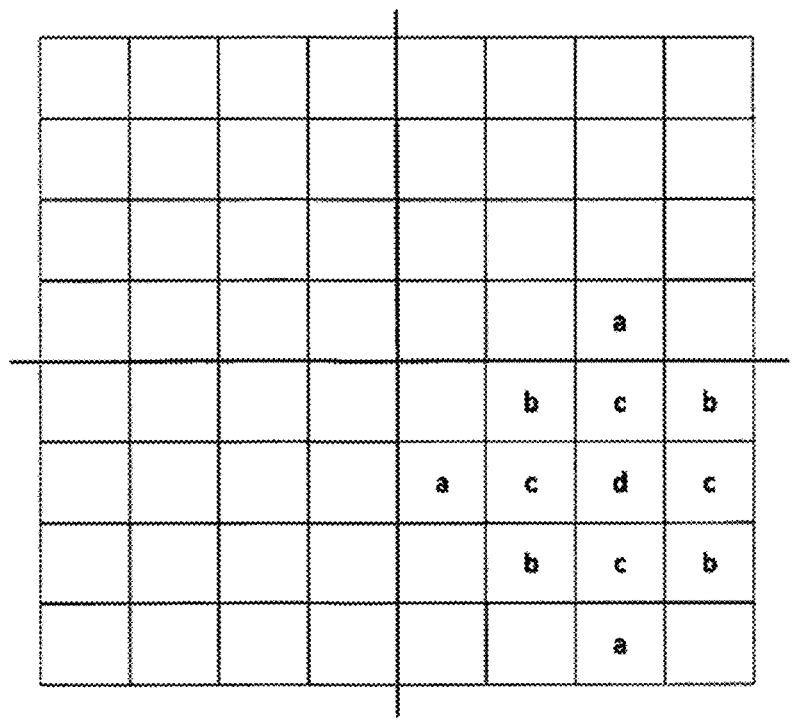
FIG. 20 provides a graphical representation of an exemplary amplitude metric, wherein the letters "a" represent a region of the metric furthest from a target area of the metric, wherein the letters "b" represent a region closer to the target area of the metric, wherein the letters "c" represent a region still closer to the target area of the metric; and wherein the letter "d" represents the target area of the metric.

Other embodiments of the disclosed system also utilize an algorithm for determining a probe alignment metric. This algorithm focuses on the center A-scans to determine the degree of proper alignment and outputs this metric as a scalar 0-100 value, where 0 represents poor alignment and 100 represents perfect alignment. It disregards any information within the data on the periphery of the field of view. As such, the algorithm only provides one-dimensional feedback and offers no information on which direction to manipulate the probe to improve alignment. The algorithm described below takes a more complex approach in providing feedback by interrogating the A-scan data for each position across the field of view to determine the live orientation and compute a remedial manipulation direction. Similar to the legacy technique, the first front-wall interface is used as an anchor for determining signal integrity. A full range gate is applied to each A-scan and the maximum amplitude and the position of that maximum amplitude are calculated ($FFWI_{MAX}$, $FFWI_{POS}$). An interrupt check is performed to ensure that the $FFWI_{POS}$ is located in the expected range. If not, the amplitude metric for that specific A-scan returns a value of 0; otherwise, the algorithm progresses. Each $FFWI_{MAX}$ value is graphically plotted according to the field of view of the sensor. Like the core algorithm for determining the fusion metric, the result can be translated into an image processing problem. For alignment, the darker pixels (higher amplitudes) represent better alignment (see FIG. 20).

Figure 21:
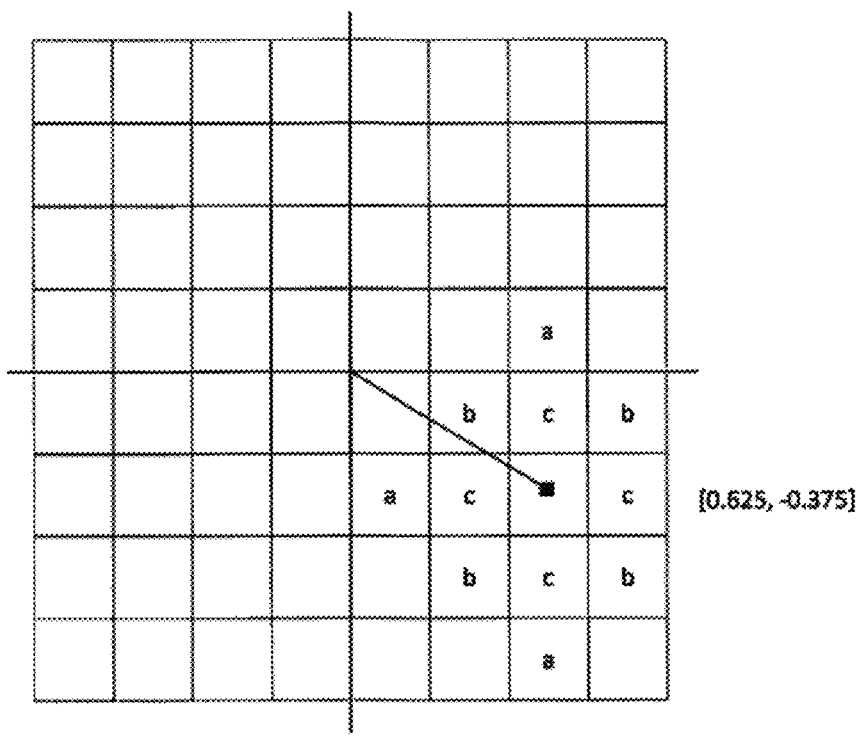
FIG. 21 provides a graphical representation of an exemplary amplitude metric, showing centroid and vector calculation, wherein the letters "a" represent a region of the metric furthest from a target area of the metric, wherein the letters "b" represent a region closer to the target area of the metric, and wherein the letters "c" represent a region still closer to the target area of the metric.

The entire image is then normalized, subtracting the minimum $FFWI_{MAX}$ value from each individual $FFWI_{MAX}$ value. Additionally, the axes, typically in engineering units (e.g. mm) is normalized, making the maximum and minimum values in each axis +1 and −1, respectively. The main spot is then found and the centroid of the spot is calculated. A vector is then drawn from the center of the field of view to the centroid of the alignment spot. Each axis component is calculated as illustrated in FIG. 21. The result is a position within an orientation quadrant, [0.625, −0.375], such as shown in FIG. 21. The feedback to the user or manipulator is to shift in the opposite direction [−0.625, −0.375].

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

What is claimed:

1. A method for characterizing a spot weld, comprising:
   (a) providing an acoustic probe, wherein the acoustic probe includes:
      (i) a plurality of ultrasonic transducer elements arranged in a curved phased array at one end of the acoustic probe, wherein the transducer elements are operative to both generate ultrasonic signals and receive reflections thereof, and
      (ii) a combination of materials for allowing the probe to conform to a contoured surface of the spot weld while enabling sound energy to be transferred directly into the spot weld under test conditions;
   (b) providing a phased array excitation unit in electrical communication with the array of the transducer elements for ultrasonically exciting the transducer elements in a phased manner;
   (c) providing a computerized controller in electrical communication with the phased array excitation unit for controlling an operation of the phased array excitation unit, and gathering and processing information from the transducer elements;
   (d) acquiring a sequence of A-scans from the phased array, wherein the A-scans describe individual portions of a field of view of the phased array,
   (e) defining an interface gate offset and length for an interface gate, and a flaw gate offset and length for a flaw gate, with respect to a known total material thickness for each individual A-scan within the sequence of A-scans;
   (f) calculating a gate ratio between a maximum amplitude under the interface gate and a maximum amplitude under the flaw gate for each individual A-scan within the sequence of A-scans;
   (g) plotting the gate ratio for each individual A-scan as a function of a location within the field of view of the phased array to generate a weld fusion map;
   (h) using a predetermined threshold to differentiate fused locations from unfused locations on the weld fusion map; and
   (i) calculating predetermined weld metrics, wherein the predetermined weld metrics include area, diameter, width, length, percent fused, or combinations thereof.

2. The method of claim 1, further comprising providing at least two sheets of material that have been joined together by resistance welding, and wherein the resistance welding has generated at least one spot weld to be characterized.

3. The method of claim 1, wherein the combination of materials further includes a flexible membrane mounted on the one end of the acoustic probe and a fluid filled chamber or solid sound delay material disposed between the membrane and the array.

4. The method of claim 1, wherein the transducer elements are further arranged into discrete subgroups, and wherein each subgroup may be activated independently of the other subgroups and at different time intervals.

5. The method of claim 4, wherein activating each subgroup independently of the other subgroups and at different time intervals for each transducer element in the subgroup provides signal focusing and steering capability.

6. The method of claim 1, wherein the interface gate offset and the flaw gate offset are adjusted according to a position of a first front surface refection position for each individual A-scan within the sequence of A-scans.

7. The method of claim 1, wherein the flaw gate offset and length are adjusted according to a measured position of the maximum amplitude under the interface gate for each individual A-scan within the sequence of A-scans.

\* \* \* \* \*